United States Patent [19]

Nyce et al.

[11] Patent Number: 5,253,522

[45] Date of Patent: Oct. 19, 1993

[54] APPARATUS FOR DETERMINING FLUID LEVEL AND FLUID DENSITY

[75] Inventors: David S. Nyce, Apex, N.C.; Jacob Tellerman, Bayside, N.Y.

[73] Assignee: MTS Systems Corporation, Minneapolis, Minn.

[21] Appl. No.: 728,359

[22] Filed: Jul. 11, 1991

[51] Int. Cl.⁵ .............................................. G01N 9/12
[52] U.S. Cl. ..................................... 73/453; 73/32 A; 73/290 V; 324/207.13
[58] Field of Search ............... 73/453, 447, 32 A, 291, 73/290 V; 324/207.13

[56] References Cited

U.S. PATENT DOCUMENTS

| | | | |
|---|---|---|---|
| 2,524,600 | 10/1950 | Raymond et al. | 73/33 |
| 3,040,585 | 6/1962 | Chatel et al. | 73/453 |
| 3,089,502 | 5/1963 | Davidson et al. | 137/90 |
| 3,126,745 | 3/1964 | Lutke | 73/453 |
| 3,154,950 | 11/1964 | Hargens, III et al. | 73/453 |
| 3,407,659 | 10/1968 | Bonnell | 73/309 |
| 3,537,085 | 10/1970 | Mayer et al. | 340/182 |
| 3,661,652 | 5/1972 | Uitenbroek | 136/182 |
| 3,898,555 | 8/1975 | Tellerman | 324/34 D |
| 3,921,461 | 11/1975 | Layton | 73/447 |
| 3,964,317 | 6/1976 | Blanchard | 73/453 |
| 3,994,174 | 11/1976 | Eckmann | 73/452 |
| 4,155,254 | 5/1979 | Colditz | 73/447 |
| 4,236,144 | 11/1980 | Sunagawa | 340/870 |
| 4,305,283 | 12/1981 | Redding | 73/290 |
| 4,361,037 | 11/1982 | Hauschild et al. | 73/295 |
| 4,503,419 | 3/1985 | Kidd et al. | 340/59 |
| 4,726,226 | 2/1988 | Tellerman | 73/292 |
| 4,939,457 | 7/1990 | Tellerman | 324/207.13 |
| 5,076,100 | 12/1991 | Hunter et al. | 324/207.13 |

OTHER PUBLICATIONS

Advertising brochure: "Temposonics Brand Liquid Level Measurement Gauges," MTS Systems Corporation, Copyright 1986.
"Hydrostatic Tank Gauging: The Intelligent Alternative to an Old Problem," Schneider et al., *ISA* 1985, pp. 1309–1320.
"New Product Introduction," Shaevitz Sensing Systems, Inc., Phoenix, Ariz., 1989.

*Primary Examiner*—John E. Chapman
*Attorney, Agent, or Firm*—Kinney & Lange

[57] ABSTRACT

A density measuring device having a float with a marker provided therein that is connected by a pair of springs to each of the two supports which are on opposite sides of the float along a guide. A sonic waveguide arrangement is provided extending along this guide past at least one of the supports which can measure the relative positions of the float to thereby determine the effective buoyant force on the float and so the density of the fluid in which the float is submerged. Use of a further float permits determining fluid levels.

21 Claims, 3 Drawing Sheets

APPARATUS FOR DETERMINING FLUID LEVEL AND FLUID DENSITY

BACKGROUND OF THE INVENTION

The present invention relates to devices for measuring densities of fluids and, more particularly, to devices for measuring such fluid densities based on buoyancy effects in the corresponding fluid.

The mass density of various kinds of fluids is an important parameter in many situations. This is because this parameter of a fluid is important in characterizing the behavior of that fluid in both static and dynamic, or flow, situations. As an example of the former, the density of a fluid stored in a storage tank is often a necessary factor to know for accurate remote sensing of the mass of that fluid. In addition, other fluid parameters may also be of interest, insofar as being simultaneously measured, such as temperature or fluid level in the tank.

A number of different kinds of densimeters have been developed for use in measuring the density of fluids. Some densimeters are of a sufficient accuracy for many needs, but are expensive. Other densimeters are more economical but fail to provide sufficient accuracy for many uses. Thus, there is a desire for an economical densimeter which can provide a high degree of accuracy in measuring the density of selected fluids and, possibly, other fluid parameters.

SUMMARY OF THE INVENTION

The present invention provides a densimeter of which at least a part can be submerged in a fluid for which the density is to be determined. This densimeter has a float means with a marker provided therewith that is connected by a pair of spring arrangements to each of two supports which are on opposite sides of the float means along a guide. A position determination means is provided extending along this guide past at least one of the supports which can measure the relative positions of the float means to thereby determine the effective buoyant force on the float means and so the density of a fluid in which the float means is submerged. This position determination means involves a sonic waveguide arrangement. A computing means capable of determining positions of the float means can be included with the position determination means. The float can be properly weighted for any particular fluid with which it is to be used so that it takes a desired point along the guide if the fluid is in a specified set of conditions. Multiple floats with corresponding supports and springs can be used along the guide if density is to be sampled at different locations, or if an average density is to be determined.

The densimeter can be used in conjunction with a liquid level float thereby allowing both the liquid level and fluid density information to be determined from a common waveguide arrangement. The densimeter can include a computing means for providing a compensated liquid level output signal adjusted for the density of the fluid.

The float means can have a position marker means provided therewith so that the position of the float means can be determined from the relative positions of the position marker and a fixed reference marker. The densimeter can have a float means that has a weight that is equal in magnitude but opposite in direction to a buoyant force acting thereon when submerged in a fluid of a given density. A computation means can translate the positions of the float means into fluid density deviations from the given fluid density.

DETAILED DESCRIPTION OF THE PREFERRED EMBODIMENTS

Figures 1, 2:
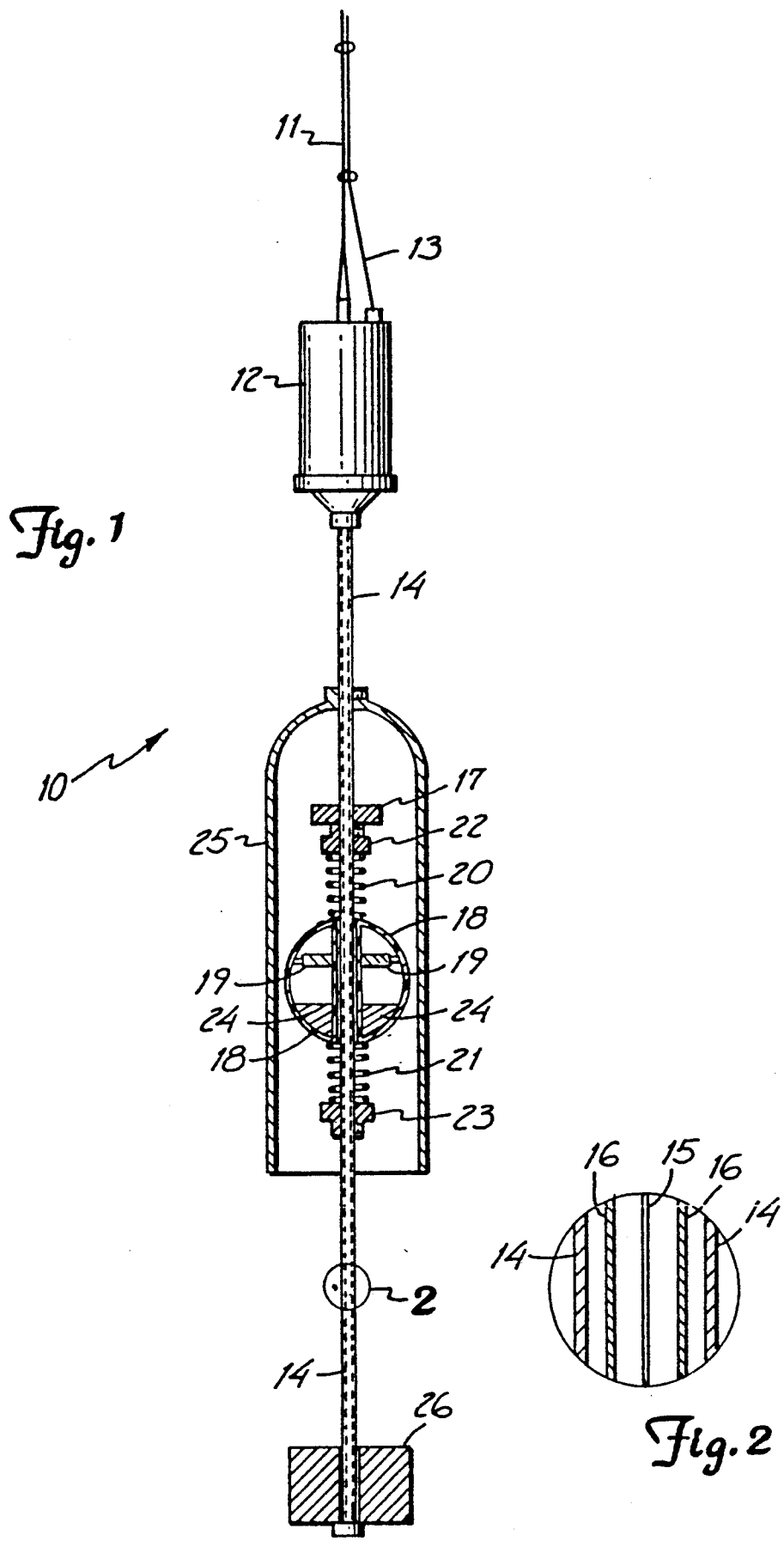
FIG. 1 shows a structure embodying the present invention.
FIG. 2 shows a fragmentary view of the structure of FIG. 1.

FIG. 1 shows a densimeter, 10, embodying the present invention. Densimeter 10 is shown suspended on a support cable, 11, one end of which is connected to the housing of a signal processing arrangement, 12, and the other end thereof being connected to a support means (not shown) from which such a suspension is made. A two-wire electrical conductor means, 13, is sufficient to provide electrical power to the electronics of signal processing arrangement 12 and to serve as a means for transmitting signals generated therein to a remote utilization site. The outer housing of signal processing arrangement 12 is typically formed of stainless steel, such as the well known alloy No. 316, and sealed against intrusions of any fluid in which densimeter 10 may be suspended for purposes of measuring its density.

Extending from the housing of signal processing arrangement 12 is a sonic waveguide housing tube, 14, also typically formed of this same stainless steel alloy and also sealed against intrusions by any fluid in which it may be immersed. A relative distance measuring apparatus is contained in the housing of signal processing arrangement 12 and sonic waveguide housing tube 14 of the kind set forth in either of U.S. Pat. No. 3,898,555 to J. Tellerman, issued Aug. 5, 1975, and U.S. Pat. No. 4,726,226 to J. Tellerman, issued Feb. 23, 1988, both of which are assigned to the assignee of the present application and both of which are incorporated herein by reference. The latter patent discloses a system in which temperature can be measured, as well as relative distance, and the temperature information so obtained may be used in the present system as a basis for providing compensation of signals having unwanted variations therein due to temperature variations. The signal processing arrangement 12 may embody various forms such as any of a microprocessor, a programmable array logic implementation, or other logic implementation. These different methods for implementing the processing arrangement 12 are all well known.

The relative distance sensing apparatus in the housing of signal processing arrangement 12 and tube 14 is based on a current pulse generator in signal processing arrangement 12 repetitively providing current pulses through the sonic waveguide. The sonic waveguide comprises a wire for conducting such current pulses mounted inside a ferromagnetic tube formed of a material exhibiting magnetostriction. Both the wire and the magnetostrictive tube together extend through the interior of tube 14. A portion of this sonic waveguide is shown in the fragmentary view of FIG. 2 in which tube 14 is shown to contain a central wire, 15, positioned in the interior of a magnetostrictive tube, 16.

The repetitive current pulses described above are transmitted along wire 15. If these current pulses traveling along wire 15 should pass through a region in which there is a relatively intense magnetic field directed along wire 15, such as due to a magnet attached to a device which can take various positions of interest to be measured along wire 15, magnetostrictive tube 16, and housing tube 14, each such current pulse will occasion a torsional stress pulse in magnetostrictive tube 16 at the location of the relatively intense magnetic field. This torsional pulse in tube 16 results because of the temporary helical total magnetic field which comes about at that location from the combining of this relatively intense field directed along the waveguide and the circular magnetic field due to the passing current pulse. The resulting torsional pulse will travel in both directions along tube 16 from that location. Such a torsion pulse on ferromagnetic tube 16 returning to signal processing arrangement 12 is sensed through a converter which converts this torsion pulse to an electrical signal. The time difference between the transmission of the current pulse on wire 15 causing such a torsion pulse, and the receiving of that torsion pulse by the converter, is a measure of the distance between the location of the relatively intense magnetic field and the signal converter in signal processing arrangement 12.

The accuracy of the determination of the location of the relatively intense magnetic field along wire 15 and tubes 14 and 16, i.e. the location of the device in the example above to which a magnet is attached, can be significantly improved with the use of a reference magnet, 17, fixedly positioned along tube 14 as is shown in FIG. 1. A current pulse down wire 15 will return both a first torsion pulse due to the reference magnet and a following, second torsion pulse due to the magnet attached to the variable position device that is to have its position determined. The time difference between the two torsional pulses will then be essentially due strictly to the positional differences of these magnets, and the absolute time difference between the time a torsional pulse is initiated by the corresponding current pulse passing the variable position device magnet and its reaching the converter need not be relied on any longer to determine the relative position of that device with respect to the converter.

This resulting ability to use the time difference between two returning torsion pulses is helpful in improving accuracy since the time duration between initiating a current pulse and the return to the converter of the resulting torsion pulse due to interaction with the device magnet is subject to greater error than is the difference in time between the returning torsion pulses due to both the reference magnet and the device magnet. This is because of variations in the electronic circuits and the like which affect the timing of the pulses produced thereby. These pulse timing variations will be essentially identical for the two torsion pulses and so will not affect the time difference therebetween to thereby avoid errors. As a result, the position of the moving magnet can be found with respect to the reference magnet which is fixed on tube 14 with significantly greater accuracy than it can be found with respect to the converter in signal processing arrangement 12.

The variable position device having an attached magnet in FIG. 1, for which the relative position is to be determined, is a float, 18, with this attached magnet being designated 19 in that figure. Float 18 is typically a spherical stainless steel structure having an opening through the center thereof through which sonic waveguide housing tube 14 extends. Magnet 19 is of a toroidal shape so that it also goes around tube 14 while being supported within float 18 such that it has a disk structure with a central perforation. The opening in float 18 to accommodate the passage of tube 14 is sufficient to allow easy movement of float 18 up and down its outer surface.

The position of float 18 along tube 14, and so along the sonic waveguide therein formed of wire 15 and magnetostrictive tube 16, is determined by a pair of helical springs, 20 and 21, a pair of stop collars, 22 and 23, and the density of the fluid in which float 18 is submerged. In effect, float 18 and springs 20 and 21 together provide a buoyant force-to-waveguide translation converter. Since the buoyant force on float 18 is a product of the volume of float 18 and the density of the fluid in which it is submerged, the force-to-translation conversion provided by float 18 and springs 20 and 21 effectively provides a density-to-translation conversion. The starting point along the waveguide, or along housing tube 14, from which the translations of float 18 are measured can be adjusted by the amount of a weighting material, 24, provided in float 18 in a quantity selected for any particular fluid in which float 18 is submerged. Weighting material 24 being present also keeps the center of gravity of float 18 below the center of buoyancy therein to aid in maintaining the dynamic stability of float 18.

Thus, weighting material 24 in float 18, which might be lead or an oil, can be chosen in sufficient mass to set the initial point of float 18 when submerged in a fluid. Conveniently, float 18 should be set to be at a point along tube 14 that is approximately centered between stop collars 22 and 23, for the fluid in which float 18 is submerged, for density measurement purposes meeting a set of specified standard conditions. In those circumstances, densimeter 10 need only measure density variations from the density value occurring in this set of standard fluid conditions (compensated as necessary for deviations of other fluid parameters from the standard conditions).

This density measurement method based on only deviations from a standard value can substantially improve the accuracy of the result obtained, as opposed to having to resolve the entire range of density from a value of zero to whatever the measured values might be. If the variation in density to be encountered is known to not be more than 10% either way from the standard condition, as an example, and the relative position of magnet 19 can be measured to an accuracy of 0.1% by the relative position apparatus in signal processing arrangement 12 including the sonic waveguide in housing tube 14, the accuracy of the density measurement can be on the order of 0.01% rather than 0.1%.

Because float 18 has housing tube 14 extend therethrough, as also occurs through helical springs 20 and 21 in each being connected between float 18 and a corresponding one of stop collars 22 and 23, float 18 can move up and down tube 14 against springs 20 and 21 without obstruction while being guided by tube 14 along the directions in which it extends. Of course, helical springs 20 and 21 can also extend and contract in these directions because of being guided along tube 14. There is no tendency for these springs to get very far out of alignment with one another during the motion thereof, or for them or float 18 to move in directions other than those along which tube 14 extends. That is, float 18 is free to move in essentially only those directions coinciding with the principal axes of these helical springs. This circumstance allows relatively low spring constants for helical springs 20 and 21 since there is no need to be concerned about lateral deflections of these springs or float 18 away from tube 14.

Relatively small spring constants are desired for helical springs 20 and 21 so that a substantial motion of float 18 will be permitted by them along tube 14 to thereby reduce errors because of hysteresis and non-linearity primarily due to springs 20 and 21. In addition, the large range of motion provides for a substantial resolution capability in densimeter 10 since distance changes of float 18 along tube 14 vary directly with the volume of float 18 and the density of the fluid, but vary inversely with the values of the spring constants. Float 18 should move at least an inch in either direction from the center point along tube 14 between stop collars 22 and 23 for the range of expected density change in the fluid being measured, and preferably two inches or more either way from this center point over this density range.

The use of both of helical springs 20 and 21, with one in contraction and one in extension for most positions of float 18 except near the center point between stop collars 22 and 23 (where both springs are typically slightly in compression), results in some of the non-linearities in each spring canceling those of the other to provide a more linear result for the translation of float 18 with fluid density variation. The effects of temperature on the coefficients of the springs can be minimized by using a material therefor which has nearly a zero temperature coefficient, as, for instance, $N_i$-Span-C springs which are well known for this purpose. Of course, to the extent that such non-linearities in springs 20 and 21, or temperature dependence of the spring constants of each, are repeatable, a microprocessor located in signal processing arrangement 12, or located at the remote utilization station, can compensate the output signal data from densimeter 10 for such errors. Similarly, other temperature induced errors, such as the changing of the volume of float 18, can be similarly compensated. Reducing errors is further promoted by the use of a Stillwell bell, 25, which aids in minimizing the effects of fluid disturbances on float 18.

Figure 3:
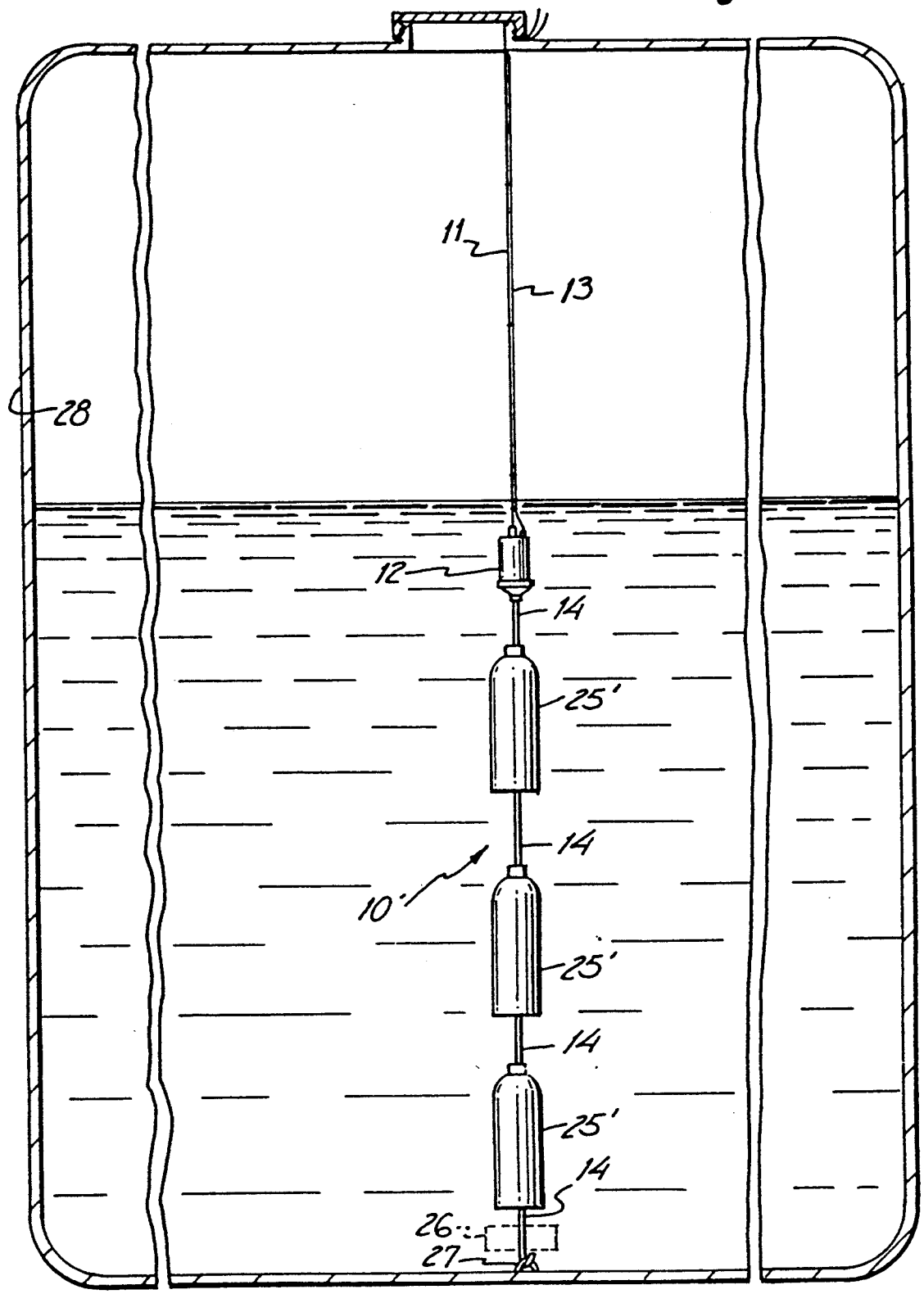
FIG. 3 shows an extended version of the structure of FIG. 1 provided in a storage tank used for storing fluids such as a liquid therein, and FIG. 4 a fragmentary view of the structure of FIG. 1 modified to be integrated into a float used to determine liquid level in a tank.

Densimeter 10, in hanging from support cable 11, is subjected to being moved about somewhat by disturbances in the fluid in which it is submerged. This can be reduced by the addition of a weight, 26, at the end of housing tube 14. An alternative shown in FIG. 3 is to connect tube 14 to a fixture, 27, connected to the bottom of a tank, 28, in which is contained the fluid upon which density measurements are to be made through having densimeter 10 submerged therein. Alternatively, as shown in FIG. 3, weight 26 could again be used as shown in dashed lines there.

Densimeter 10 of FIG. 1 is redesignated densimeter 10' in FIG. 3 because of the addition of two further bells, here all designated 25', along housing tube 14. Each of bells 25' contains therein just what is shown contained within bell 25 of FIG. 1, including a float, a pair of helical springs, a pair of stop collars and a reference magnet. In this arrangement, densities of the tank-contained fluid can be found at three different locations therein. This is useful for those kinds of fluids in which there is the possibility of density variation. In such instances, the three different density measurements can be averaged by either a microprocessor in signal processing arrangement 12 or by some suitable computer or other means located at the utilization site to which signal conductor 13 extends to obtain the average density of the fluid in tank 28.

In operating densimeter 10', repetitive current pulses are again provided on a wire in the sonic waveguide provided in housing tube 14 thereof equivalent to wire 15 in the sonic waveguide in tube housing 14 of densimeter 10 of FIGS. 1 and 2. Each such current pulse passes by the reference magnet and the float magnet contained in each of bells 25'. A magnetostrictive tube surrounding that wire, again one equivalent to tube 16 in the sonic waveguide in tube housing 14 of densimeter 10 of FIGS. 1 and 2, will have torsion pulses successively generated therein for each one of these current pulses passing these successive magnets encountered along housing tube 14 as that pulse translates along the wire contained therein. As a result, each such current pulse will lead to three successive pairs of torsion pulses translating along the magnetostrictive tube to the converter in signal processing arrangement 12 with the time difference between each pair being a measure of the density of the fluid occurring at each of the floats in the bells 25' thus providing the desired information.

Figure 4:
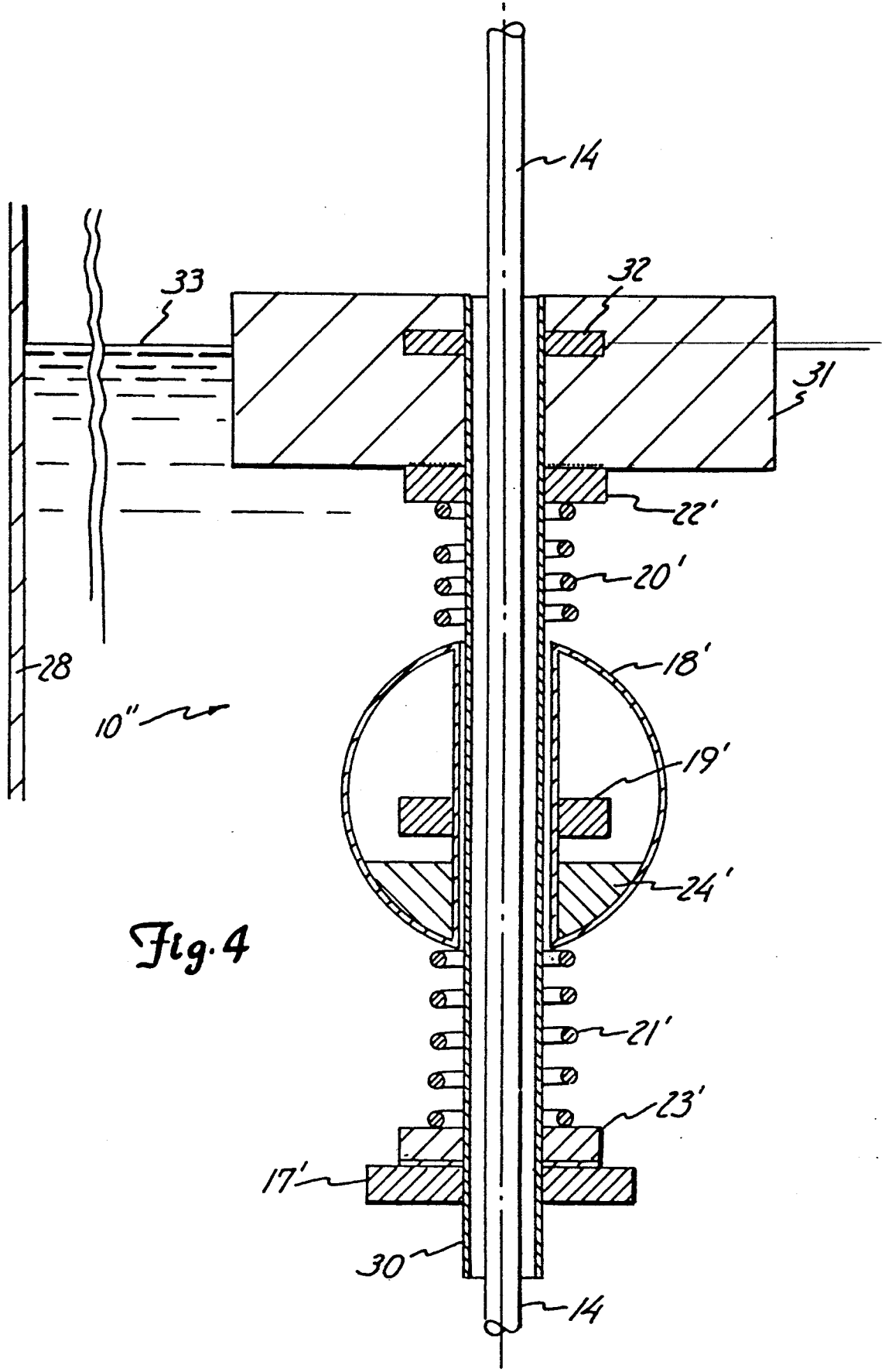

Densimeter 10 of FIG. 1 is redesignated densimeter 10" in FIG. 4 because of the addition of density sensor tube, 30, liquid level float, 31, and level float magnet, 32. Densimeter 10" contains therein just what is shown contained in densimeter 10 of FIG. 1, including a density determination float, a pair of helical springs, a pair of stop collars and a reference magnet. Densimeter 10" has a sonic waveguide housing tube 14 that extends into tank 28 similar to densimeter 10. Density sensor tube 30 has an inside diameter that is greater than the outside diameter of housing tube 14 such that the density sensor tube 30 moves freely along housing tube 14. Liquid level float 31 has an opening in its center to accommodate the density sensor tube 30 about tube 14, float 31 being fixedly attached to tube 30. Liquid level float 31 has positive buoyancy so as to stay positioned at the surface, 33, of the liquid fluid within tank 28. As the upper liquid surface, or fluid level, 33 is raised or lowered, level float 31 and density sensor tube 30 move correspondingly up and down along housing tube 14.

Stop collars 22', 23', springs 20' and 21', and densimeter float 18' are positioned on density sensor tube 30 just as stop collars 22, 23, springs 20 and 21, and float 18 were positioned on housing tube 14 in densimeter 10 shown in FIG. 1. Stop collar 22' is attached to liquid level float 31. Reference magnet 17' is attached to density sensor tube 30 for determining relative changes of position of densimeter float 18' similar to reference magnet 17 and densimeter float 18 of densimeter 10. Level float magnet 32 is fixedly attached to liquid level float 31. Level float magnet 32 is of a toroidal shape so that it goes around density sensor tube 30.

Level float magnet 32 in liquid level float 31 is used for determining the distance between liquid level 33 and signal processing arrangement 12. Fluid level 33 in tank 28 is determined by subtracting (a) the distance between level float magnet 32 and signal processing arrangement 12, from (b) the known, or previously measured, distance between signal processing arrangement 12 and the bottom of tank 28.

The combined weight of reference magnet 17', springs 20', 21' and stop collars 22', 23' causes liquid level float 31 to be partially immersed to differing depths in the liquid contained in tank 28 with varying liquid density, and thus provides a source of error in the measurement of fluid level 33. Densimeter float 18', however, contributes little to this source of error because its weight is almost completely counteracted by the liquid buoyant force, and therefor contributes little weight to liquid level float 31. Errors resulting from liquid level float 31 being partially immersed to different degrees with the changing density of the fluid contained in tank 28 can be compensated by the microprocessor in signal processing arrangement 12 because the density of the fluid is available through measurement thereof based on densimeter float 18'. Therefore, an advantage of this arrangement is that fluid level 33 and the density of the fluid in tank 28 can thus both be determined using a common waveguide housing tube 14, thereby reducing equipment costs as well as labor costs for installation of instrumentation with such capabilities.

In operating densimeter 10'', repetitive current pulses are again provided on a wire, or wire-like structure, 15 in densimeter 10, located in sonic waveguide 16 provided in housing tube 14, as they were in densimeter 10. Each such current pulse passes by level float magnet 32, densimeter float magnet 19', and reference magnet 17' contained in densimeter 10''. Each current pulse leads to three torsion pulses translating along the magnetostrictive tube of sonic waveguide 16 to the converter in signal process arrangement 12. The time difference between the transmittal of a current pulse and the receipt of the corresponding first torsion pulse is a measure of the distance between level float magnet 32 and signal processing arrangement 12. The time difference between the next two pulses is the measure of the density of the fluid occurring about densimeter float 18'. Signal processing equipment 12 is then able to compute the desired fluid level and fluid density information.

Having thus described the invention, it should be clear that many changes could be made to the described embodiment without departing from the spirit and scope of the invention. For example, liquid level float 31, shown in FIG. 4, having level float magnet 32 attached thereto, may be separated from the densimeter 10''. This liquid level float 31, and level float magnet 32 may then be used with densimeter 10, shown in FIG. 1, such that the liquid level float 31 is freely movable along housing tube 14 with densimeter 10 fixedly mounted to housing tube 14. Densimeter 10 is fixedly mounted to tube 14 at a point below the lowest measured liquid level excursion thereby allowing liquid level float 31 to move up and down along tube 14 with changes in liquid levels in tank 28. This arrangement allows for both the density of the fluid in tank 28 and the fluid level 33 to be determined using a common waveguide housing tube 14. In yet another arrangement of the present invention, densimeter 10'' and densimeter 10 are both mounted on the same waveguide housing tube 14. Densimeter 10'' is movably mounted to tube 14 for determining the liquid level and the liquid density near the liquid surface and densimeter 10 is fixedly mounted to tube 14 for determining the liquid density at some fixed level in tank 28. Both of these arrangements make use of a common waveguide and thereby reduce equipment costs as well as labor costs for installation of instrumentation with such capabilities.

Although the present invention has been described with reference to preferred embodiments, workers skilled in the art will recognize that changes may be made in form and detail without departing from the spirit and scope of the invention.

What is claimed is:

1. An apparatus capable of determining fluid level and fluid density in which at least portions thereof are submerged, said apparatus comprising:
   a first float means submergible in said fluid and having a first position marker means provided therewith, said first float means being provided along a guide means between a first pair of support means;
   a first pair of axial translational force means each having a pair of ends and each being capable of being extended or contracted in length between said ends along a primary axis thereof to an extent depending on magnitudes of axial forces exerted therebetween, said first pair of axial translational force means each having one said end thereof connected to said first float means and each having that remaining said end thereof connected to a different one of said first pair of support means;
   a position determination means extending at least in part along said guide means past one of said first pair of support means, said position determination means being capable of measuring relative positions of said first marker means between said first pair of support means; and
   a second float means for providing an output signal indicative of a level of said fluid within a container, said second float means being at least partially exposed outside said fluid within said container and having a second position marker means provided therewith, said position determination means being capable of measuring the position of said second position marker means within said container.

2. The apparatus of claim 1 wherein said second float means is attached to said guide means with said guide means being moveable relative to said position determination means.

3. The apparatus of claim 1 wherein said position determination means includes a computing means for providing a compensated output signal adjusted for said density of said fluid.

4. The apparatus of claim 2 wherein said position determination means includes a sonic waveguide extending into said guide means with each of said pair of support means being mounted to said guide means, means for providing torsion on said sonic waveguide and a torsion detection means for detecting torsion along said sonic waveguide.

5. The apparatus of claim 4 wherein said position determination means further comprises an elapsed time duration measurement means for measuring time durations begun by initiating selected electrical pulses to translate along said sonic waveguide and terminated by having corresponding torsional pulses translating along said sonic waveguide detected by said torsion detection means.

6. The apparatus of claim 1 wherein said second marker means is a magnet.

7. The apparatus of claim 4 wherein said guide means is a first tube means at least partially enclosing a first elongate space and said waveguide is a second tube means at least partially enclosing a second elongate space.

8. The apparatus of claim 7 wherein said second tube means extends at least partially into said first tube means, said first tube means being freely movable about said second tube means.

9. The apparatus of claim 4 wherein said position determination means is mounted on said sonic waveguide.

10. The apparatus of claim 1 wherein said second float means is movable relative to said position determination means and each of said first pair of support means is fixed relative to said position determination means.

11. An apparatus capable of determining fluid level and fluid density in which at least portions thereof are submerged, said apparatus comprising:
- a first float means submergible in said fluid and having a first position marker means provided therewith, said first float means being provided along a guide means with said guide means and said first float means having a compliant member attached therebetween so that said first float means can be moved under buoyant force relative to said guide means;
- a second float means at least partially exposed outside said fluid within a container and having a second position marker means provided therewith, said second float means provided along said guide means with said second float means position indicative of fluid level; and
- a position determination means extending at least in part along said guide means for determining positions of said first position marker means and said second position marker means, said position determination means including a computing means for providing representing at least one of said fluid density and said fluid level.

12. The apparatus of claim 11 wherein said compliant member is a first pair of axial translational force means each having a pair of ends and each being capable of being extended or contracted in length between said ends along a primary axis thereof to an extent depending on magnitudes of axial forces exerted therebetween, said first pair of axial translational force means each having one said end thereof connected to said first float means and each having that remaining said end thereof connected to a different one of a first pair of support means.

13. The apparatus of claim 11 wherein said second float means is attached to said guide means with said guide means being moveable relative to said position determination means.

14. The apparatus of claim 11 wherein said computing means includes an output therein for providing a compensated output signal adjusted for said density of said fluid.

15. The apparatus of claim 13 wherein said position determination means includes a sonic waveguide extending into said guide means with said compliant member being mounted to said guide means, means for providing torsion on said sonic waveguide and a torsion detection means for detecting torsion along said waveguide.

16. The apparatus of claim 15 wherein said position determination means further comprises an elapsed time duration measurement means for measuring time durations begun by initiating selected electrical pulses to translate on a conductor along said sonic waveguide and terminated by having corresponding torsional pulses translating along said sonic waveguide detected by said torsion detection means.

17. The apparatus of claim 11 wherein said first position marker means is a magnet as is said second position marker means.

18. The apparatus of claim 15 wherein said guide means is a first tube means at least partially enclosing a first elongate space and said waveguide is a second tube means at least partially enclosing a second elongate space.

19. The apparatus of claim 18 wherein said second tube means extends at least partially into said first tue means, said first tube means being freely movable about said second tube means.

20. The apparatus of claim 15 wherein said position determination means is mounted on said sonic waveguide.

21. The apparatus of claim 12 wherein said second float means is movable relative to said position determination means and each of said first pair of support means is fixed relative to said position determination means.

* * * * *

UNITED STATES PATENT AND TRADEMARK OFFICE
CERTIFICATE OF CORRECTION

PATENT NO. : 5,253,522

DATED : October 19, 1993

INVENTOR(S) : DAVID S. NYCE, JACOB TELLERMAN

It is certified that error appears in the above-identified patent and that said Letters Patent is hereby corrected as shown below:

Col. 10, line 31, delete "tue", insert --tube--

Signed and Sealed this

Twelfth Day of April, 1994

Attest:

BRUCE LEHMAN

*Attesting Officer*     *Commissioner of Patents and Trademarks*